(12) United States Patent
Adachi (10) Patent No.: US 6,478,732 B2
(45) Date of Patent: Nov. 12, 2002

(54) ENDOSCOPE SYSTEM (75) Inventor: Rensuke Adachi, Tokyo (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/919,968

(22) Filed: Aug. 2, 2001

(65) Prior Publication Data

US 2002/0022766 A1 Feb. 21, 2002

(30) Foreign Application Priority Data

Aug. 8, 2000 (JP) .................................. 2000-239925

(51) Int. Cl.$^7$ ................................................ A61B 1/06
(52) U.S. Cl. ...................................... 600/178; 600/181
(58) Field of Search .................................. 600/178, 181; 348/68, 70; 362/574

(56) References Cited

U.S. PATENT DOCUMENTS

| | | | |
|---|---|---|---|
| 4,974,076 A | * 11/1990 | Nakamura et al. | ............ 348/71 |
| 5,408,263 A | * 4/1995 | Kikuchi et al. | .......... 348/223.1 |
| 5,772,580 A | 6/1998 | Utsui et al. | |
| 5,855,595 A | 1/1999 | Fujishima et al. | |

FOREIGN PATENT DOCUMENTS

WO 99/37204 7/1999

* cited by examiner

*Primary Examiner*—John Mulcahy
(74) *Attorney, Agent, or Firm*—Greenblum & Bernstein, P.L.C.

(57) ABSTRACT

Light emitted from a light source is converted into ultraviolet-and-blue light, green light, and red light, in that order, by a first wheel. When a second wheel inserts a transparent member 251 into the optical path, the ultraviolet-and-blue light, the green light, and the red light enter a light guide. On the other hand, when the second wheel inserts a fluorescence observation filter into the optical path, ultraviolet-and-blue light is converted to ultraviolet light and then enters the light guide, while the green light is blocked and the red light enters the light guide.

7 Claims, 10 Drawing Sheets

ENDOSCOPE SYSTEM

BACKGROUND OF THE INVENTION

1. Field of the Invention

The present invention relates to an endoscope system that picks up images of inside of a hollow organ based on autofluorescence generated from living tissue, acquiring image data used to determine whether the living tissue is biologically normal or abnormal. The present disclosure relates to subject matter contained in Japanese Patent Application No. 2000-239925 (filed on Aug. 8, 2000), which is expressly incorporated herein by reference in its entirety.

2. Description of the Related Art

Figure 14:
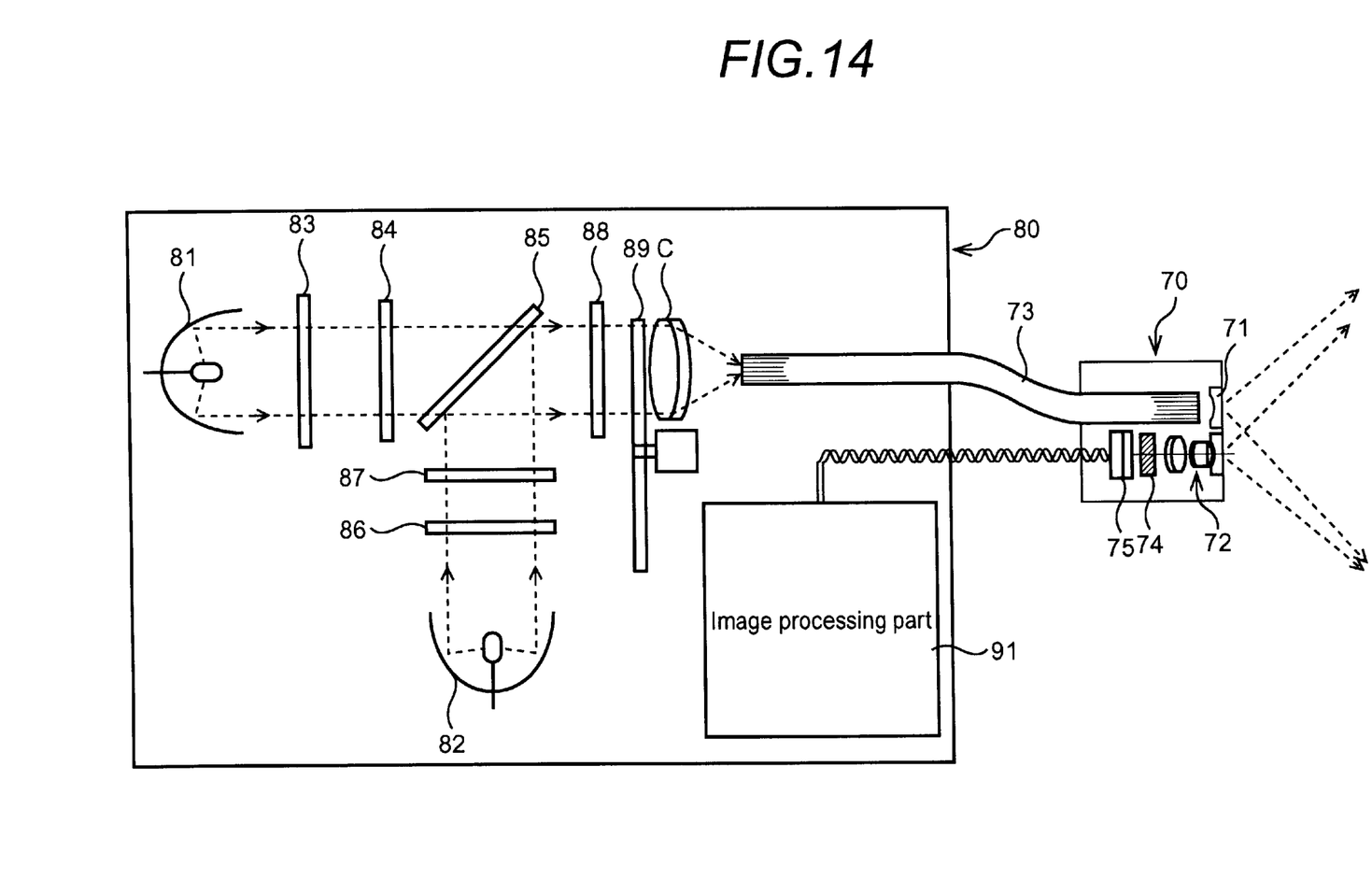
FIG. 14 is a block diagram showing scheme of the conventional endoscope device.

FIG. 14 is a block diagram of a conventional endoscope system. The endoscope system is composed of an endoscope 70 and an external unit 80. The endoscope 70 has a light distribution lens 71 and an objective lens 72 installed at its distal end. Additionally, this endoscope 70 has a light guide 73 that is a fiber bundle. The light guide 73 is led through the endoscope 70, such that its distal end faces a light distribution lens 71, while its proximal end is arranged to lead into the interior of the external unit 80. Further, the endoscope 70 is installed with an ultraviolet-and-infrared cut-off filter 74 and a CCD (charge-coupled device) 75. An imaging plane of this CCD 75 is arranged near a point at which objective lens 72 focuses an image of a subject when the distal end of the endoscope 1 is placed to face the subject. The ultraviolet-and-infrared cut-off filter 74 is set in an optical path between the objective lens 72 and the CCD 75.

The external unit 80 comprises a white light source 81 for emitting white light as a collimated light beam and an excitation light source 82 for emitting a collimated light beam, including wavelength components in the ultraviolet region. Along the optical path of the white light emitted from the white light source 81 are provided an infrared cut-off filter 83, a first shutter 84, and a dichroic mirror 85, arranged in this sequence. The infrared cut-off filter 83 blocks wavelength components in an infrared spectrum of the white light emitted from the white light source 81, at same time transmits wavelength components in a visible spectrum. The first shutter 84 intermittently blocks or transmits the white light that has passed through infrared cut-off filter 83. The dichroic mirror 85 transmits wavelength components in the visible spectrum of the light entering thereto, while reflecting wavelength components in the ultraviolet spectrum of the light. Thus, the white light in the visible spectrum that has passed through the first shutter 84 then passes through the dichroic mirror 85.

The excitation light source 82 is arranged so that light emitted therefrom orthogonally crosses the optical path of the white light passing through the dichroic mirror 85. Along the optical path between this excitation light source 82 and the dichroic mirror 85 are provided an excitation light filter 86 and a second shutter 87, arranged in this sequence from the excitation light source 82. The excitation light filter 86 transmits only those wavelength components in the spectrum that can be used as excitation light. Note that the excitation light refers to ultraviolet light capable of exciting living tissue to cause autofluorescence. The second shutter 87 intermittently blocks or transmits the excitation light that has passed through the excitation light filter 86. The excitation light that has passed through this second shutter 87 is reflected by the dichroic mirror 85, and the optical path of the excitation light reflected by the dichroic mirror 85 coincides with the optical path of the white light that has passed through this dichroic mirror 85.

In the optical path downstream of the dichroic mirror 85 are provided a diaphragm 88, a wheel 89, and a condenser lens C, arranged in this sequence. The diaphragm 88 controls the quantity of light passing therethrough. The wheel 89 is formed in a disc shape, on which four openings (not shown in the figure) are formed along its circumference. Into each of these openings are fitted a blue filter transmitting only blue light, a green filter transmitting only green light, a red filter transmitting only red light, and a transparent member transmitting the excitation light, respectively. Rotated by a motor, this wheel 89 repeatedly inserts the blue, green, and red filters and the transparent member into the optical path in sequence.

During the interval for which any one of the blue, green, or red filters of this wheel 89 is inserted into the optical path, the first shutter 84 transmits the white light while the second shutter 87 blocks the excitation light. Thus, in these times, only white light enters the dichroic mirror 85. This white light is then adjusted in amount of light by the diaphragm 88, sequentially converted into blue light, green light and red light by the blue filter, green filter and red filter of wheel 89 respectively, and enters the condenser lens C. On the other hand, during the interval for which the transparent member of this wheel 89 is inserted into the optical path, the first shutter 84 blocks the white light while the second shutter 87 transmits the excitation light, so that only the excitation light enters the dichroic mirror 85. The excitation light is then adjusted in amount of light by the diaphragm 88, passes through the transparent member of the wheel 89 and enters the condenser lens C.

This condenser C converges the light falling thereon onto the proximal end face of the light guide 73. Accordingly, the blue light, green light, red light and the excitation light repeatedly enter this light guide 73 in sequence. Light entering the light guide 73 is guided thereby and distributed by the light distribution lens 71. When the distal end of the endoscope 1 is positioned to face the subject, this subject is sequentially illuminated or irradiated by the blue light, the green light, the red light and the excitation light. Whenever this subject is illuminated by the blue light, the green light or the red light, the objective lens 72 forms an image of the subject by the blue light, the, green light or the red light in a plane with the imaging plane of the CCD 75. These images are converted into image signals by the CCD 75. More specifically, the images of the subject respectively formed from the blue light, the green light and the red light are converted into blue, green, and red image signals, respectively.

The subject generates autofluorescence when irradiated by excitation light. The autofluorescence generated from the subject and excitation light reflected by surface of the subject enters the objective lens 72, which forms an image of the subject on the imaging plane of the CCD 75. Note that, since the ultraviolet-and-infrared cut-off filter 74 is set in the optical path between the objective lens 72 and the CCD 75, the image that consists only of the autofluorescence form the subject is focused onto the imaging plane. This CCD 75 converts an image of the subject formed from the autofluorescence into an image signal (a fluorescence image signal).

Further, the external unit 80 has an image processing part 91 connected to the CCD 75 through signal wires. This image processing part 91 receives blue, green, red and fluorescence image signals output from the CCD 75 in sequence. This image processing part 91 synthesizes a color image of the subject (normal image) based on the blue, green and red image signals. Moreover, this image processing part 91 generates a fluorescence image of the subject based on the fluorescence image signal.

Thus, the conventional endoscope system has two light sources 81, 82 for emitting visible light (blue, green, and red light) and excitation light. More specifically, the conventional endoscope system has a normal light source 81 for emitting white light and an excitation light source 82 for emitting excitation light. Normally, these two light sources 81, 82 are both turned on continuously. Note that light sources 81, 82 have greater electricity requirements than other endoscope components, which makes it difficult to reduce the power requirements of such endoscope system that includes two light sources 81, 82.

Further, in this endoscope, since the light flux emitted from the two light sources is introduced to single light guide 73, a fixed space is required to implement the optical system, which frustrates efforts to reduce the bulk of the endoscope device.

BRIEF SUMMARY OF THE INVENTION

It is the object of the present invention to provide an endoscope system with a single light source capable of alternately irradiating the subject with illumination light for acquisition of color images and with irradiation light for acquisition of fluorescence images.

The endoscope system according to the present invention comprises a light source for emitting light, including visible wavelength components and an ultraviolet wavelength component to excite autofluorescence from living tissue, a light guide arranged along an optical path of the light emitted from the light source that guides the light to irradiate a subject, a first filter mechanism that has a first filter transmitting ultraviolet light and first color light which is one of blue, green and red light, a second filter transmitting second color light which is one of the red, green and blue light other than the first color light and a third filter transmitting third color light which is remain of the red, green and blue light and that sequentially and repeatedly inserts the filters into the optical path between the light source and the light guide, a second filter mechanism that intermittently inserts a fluorescence observation filter transmitting ultraviolet light, while blocking the first color light into the optical path between the light source and the light guide, an objective optical system for forming an image of the subject surface by focusing wavelength components except the ultraviolet light from the subject irradiated by the light guide, an imaging device that picks up the image of the subject formed by the objective optical system and converts it into a image signal, and a processor. The processor generates normal image data that is color image data, based on the image signals obtained by the imaging device during a period in which the first filter is inserted into the optical path, during a period in which the second filter is inserted into the optical path, and during a period in which the third filter is inserted into the optical path, respectively, while controlling the first filter mechanism with the fluorescence observation filter retracted from the optical path, and also generates fluorescence image data based on image signals obtained by the imaging device during a period in which the first filter is inserted into the optical path while controlling the first filter mechanism with the fluorescence observation filter inserted into the optical path.

The first filter mechanism and the second filter mechanism may be arranged along the optical path in this order from the light source side. In this case, light emitted from the light source is converted into a mixture of ultraviolet light and the first color light, the second color light, and the third color light, in order. While the second filter mechanism retracts the fluorescence observation filter from the optical path, the mixture of the ultraviolet light and the first color light, the second color light, and the third color light, which have passed through the first filter mechanism, are guided by the light guide to irradiate the subject. During the period in which this subject is irradiated or illuminated by the mixture of the ultraviolet light and the first color light, the second color light, the third color light in order, normal subject image data is obtained as color image data, based on image signals obtained by the imaging device. On the other hand, when the second filter mechanism inserts the fluorescence observation filter into the optical path, the mixture of the ultraviolet light and the first color light which has passed through the first filter mechanism is filtered to be pure ultraviolet light and enters the light guide. During the period in which this subject is irradiated by the ultraviolet light, fluorescence image data for the subject is obtained based on image signals obtained by the imaging device.

Alternatively, the second filter mechanism and the first filter mechanism may be arranged along the optical path in this order from the light source side. In this case, whenever the second filter mechanism retracts the fluorescence observation filter from the optical path, the mixture of the ultraviolet light and the first color light, the second color light, and the third color light enter the light guide in order. On the other hand, when the second filter mechanism inserts the fluorescence observation filter into the optical path while the first filter mechanism at the same time inserts the first filter into the optical path, ultraviolet light enters the light guide.

Incidentally, the objective optical system may have a filter for blocking ultraviolet light and an objective lens. Additionally, the filter in such an objective optical system may be an ultraviolet-and-infrared cut-off filter, transmitting visible light while blocking ultraviolet and infrared light.

Further, the fluorescence observation filter may be a filter transmitting the ultraviolet light and either light selected from the second color light and the third color light. In this case, the processor is capable of generating a reference image data based on the image signal obtained by the imaging device during the period in which the second filter or third filter is inserted into the optical path, while controlling the first filter mechanism, with the fluorescence observation filter inserted into the optical path. The processor can then extract specific image data by subtracting the reference image data from the fluorescence image data, and generate diagnostic image data by superimposing the specific image data on the normal image data. Incidentally, this system can be configured to display the portion of the diagnostic image data which corresponds to the specific image data in a specific color, for example, blue on the monitor.

Further, the first filter mechanism may have a first wheel formed in a discal shape into which the first, second, and third filters are fitted, respectively, along its circumference. Moreover, the first filter mechanism may have a motor for rotating the first wheel. Furthermore, the first filter mechanism may sequentially insert each of the filters on the first wheel into the optical path by rotation of the first wheel.

Incidentally, in case the imaging device is a CCD, the illumination time for the illumination light may be adjusted in accordance with the sensitivity of this CCD which varies with the wavelength of the incident light. More specifically, the circumferential length of the filter may be set to compensate the variation of spectral sensitivities of the CCD.

Further, the second filter mechanism may have a second wheel also formed in a discal shape on which the fluorescence observation filter and an opening are disposed along its circumference. Moreover, the second filter mechanism may be equipped with a motor for rotating the second wheel. The second filter mechanism may have a function for sequentially inserting the fluorescence observation filter and the opening into the optical path by rotation of the second wheel.

Incidentally, the light source may be consisted of a lamp and a reflector, or other type of light source. Alternatively, the light source may be composed of light emitting diodes. Further, this endoscope system may have a display device capable of displaying moving picture based on image data selected from normal image data, fluorescence image data, specific image data, and diagnostic image data.

The invention will be described below in detail with reference to the accompanying drawings in which.

DETAILED DESCRIPTION OF THE INVENTION

Figure 1:
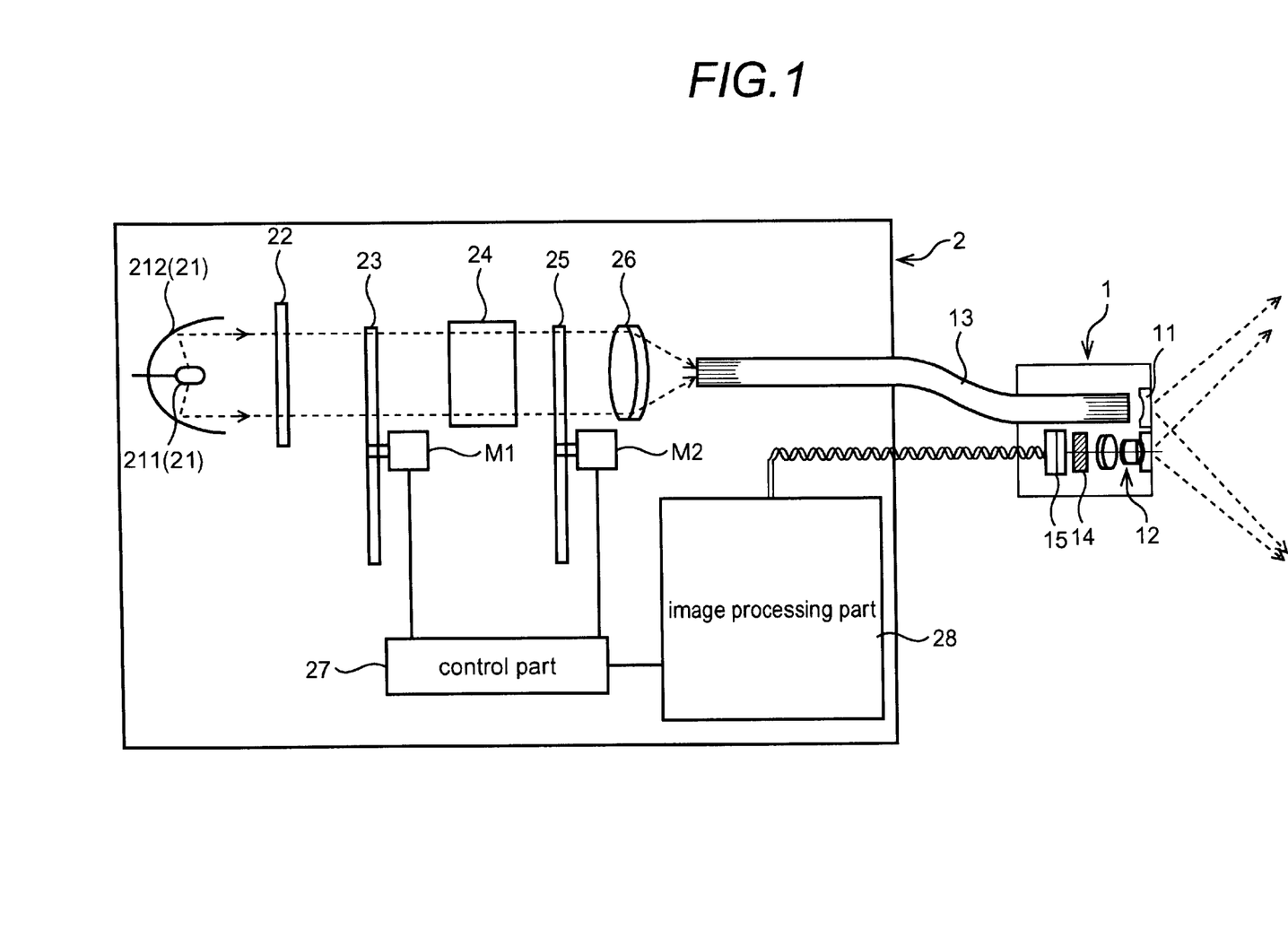
FIG. 1 is a block diagram showing a scheme of the endoscope system according to one embodiment of the present invention.

One embodiment of the endoscope system according to the present invention will be described with reference to the drawings. FIG. 1 is a block diagram of the endoscope system according to this embodiment. As shown in FIG. 1, the endoscope system is composed of an endoscope 1 and an external unit 2.

Figure 2:
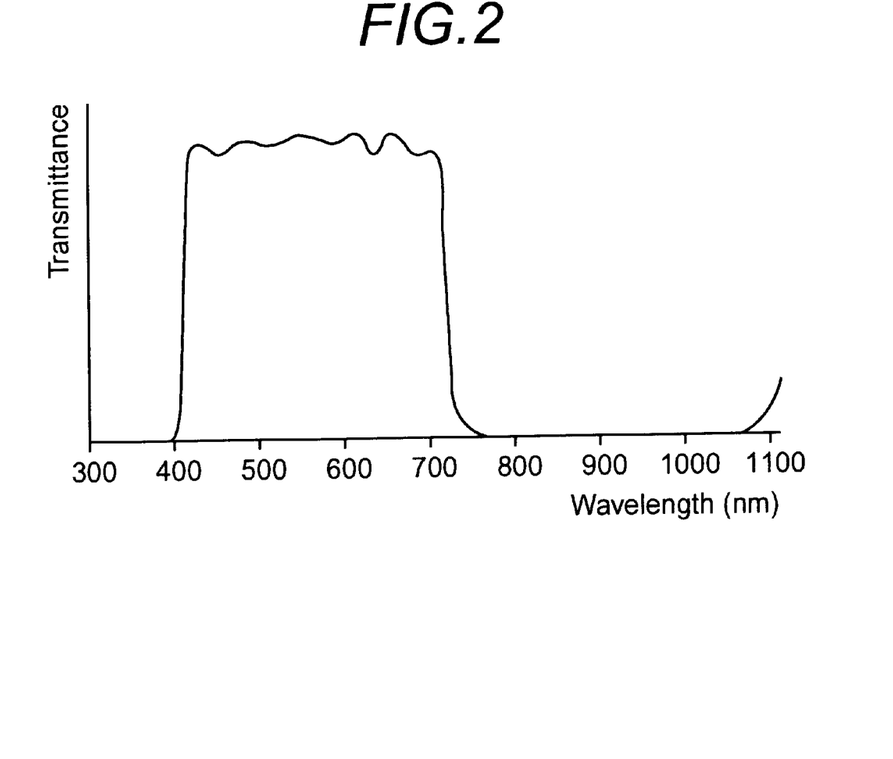
FIG. 2 is a graph showing the spectral characteristics of the ultraviolet-and-infrared cut-off filter.

Although a concrete structure of the endoscope 1 is not shown in FIG. 1, the endoscope 1 has an insertion part in the form of a flexible tube, which is inserted into the living body, an operating part connected to a proximal end of this insertion part in integrated form, and a light-guide flexible tube that is connected between this operating part and the external unit 2. A distal end of the insertion part of the endoscope 1 is provided with a tip member (not shown in the figure) made of a hard material. A bending mechanism (not shown in the figure) is built into a predetermined area near the distal end of this insertion part, and this bending mechanism causes the aforementioned area to flex. The operating part is provided with a dial for controlling the bending mechanism and with various types of operating switches. The endoscope 1 has a light distribution lens 11 and an objective lens 12, both of which are installed in the tip member thereof, respectively. The endoscope 1 has a light guide 13 which is a fiber bundle consisting of a number of multimode optical fibers bundled together. The light guide 13 is led through the insertion part, the operating part, and the light-guide flexible tube, with its distal end face facing the light distribution lens 11, and with its proximal end is inserted into the external unit 2. Further, this endoscope 1 has an ultraviolet-and-infrared cut-off filter 14 and a CCD (charge-coupled device) 15 as an imaging device. An imaging plane of this CCD 15 is set at a position where the objective lens 12 forms the image of the subject when the distal end of the endoscope 1 faces the subject of examination. The ultraviolet-and-infrared cut-off filter 14 is set in the optical path between the objective lens 12 and the CCD 15. These optics, the objective lens 12 and the ultraviolet-and-red cut-off filter 14 function as an objective optical system. FIG. 2 is a graph showing the spectral characteristics of the ultraviolet-and-red cut-off filter 14. As shown in FIG. 2, this ultraviolet-and-red cut-off filter 14 transmits visible light of wavelengths between 410 nm and 700 nm while blocking both ultraviolet light of wavelengths between 350 nm and 380 nm, which is used as excitation light, and infrared light of wavelengths between 750 nm and 1070 nm, which is used for laser therapy.

The external unit 2 has a built-in light source 21 composed of a lamp 211 and a reflector 212. This lamp 211 emits light, including wavelength components in the spectrum used for excitation light and in the visible spectrum. Incidentally, for this lamp 211, a lamp of various types, including a mercury lamp, a xenon lamp, a metal halide lamp, or the like is used. An internal surface (reflective surface) of the reflector 212 is formed as a paraboloid. The lamp 211 is disposed at the focal position of the paraboloid of the reflector 212. Under this arrangement, light emitted from the lamp 211 is converted into collimated light by the reflector 212 and is emitted from light source 21 as a collimated beam. Along the optical path of the light emitted from light source 21 are provided a light source filter 22, a first wheel 23, a diaphragm 24, a second wheel 25, and a condenser lens 26, arranged in this sequence.

Figure 3:
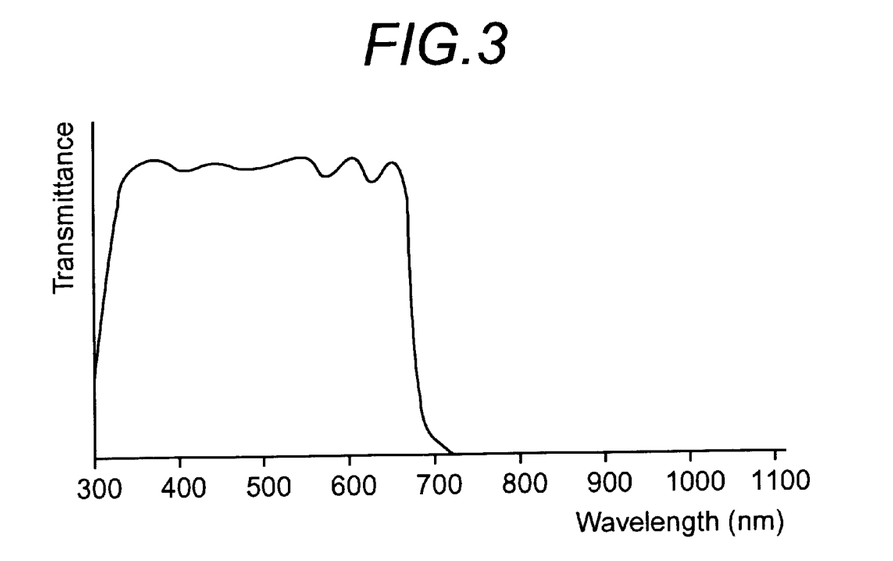
FIG. 3 is a graph showing the spectral characteristics of the light source filter.

FIG. 3 is a graph showing the spectral characteristics of the light source filter 22. As shown in FIG. 3, light source filter 22 transmits ultraviolet light and visible light, each having wavelengths between 360 nm and 650 nm, while blocking infrared light of wavelengths between 700 nm and 1100 nm. Heat radiated from the light source 21 as infrared radiation is blocked by light source filter 22 to be prevented from transmission along the optical path beyond the light source filter 22. The ultraviolet light and the visible light that have passed through this light source filter 22 travels to the first wheel 23.

Figure 4:
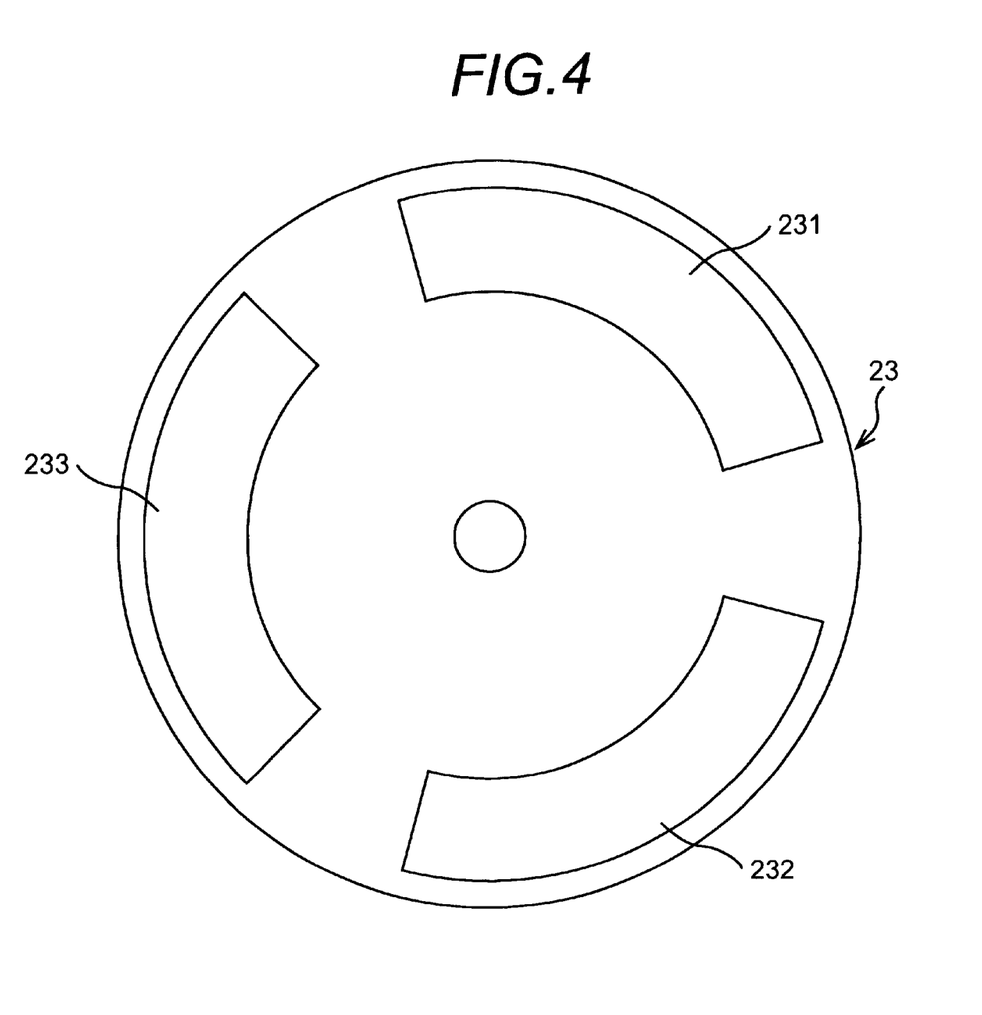
FIG. 4 is a front view of the first wheel.
Figure 5A:
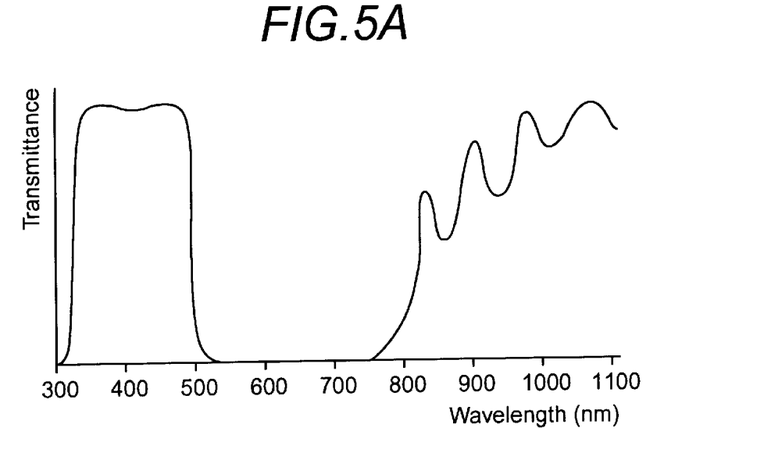
FIGS. 5A, 5B, and 5C are graphs showing the spectral characteristics of the filters in the first wheel.
Figure 5B:
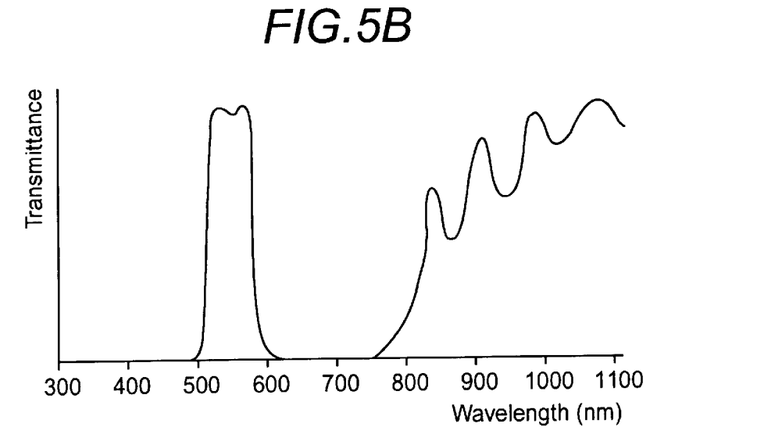
Figure 5C:
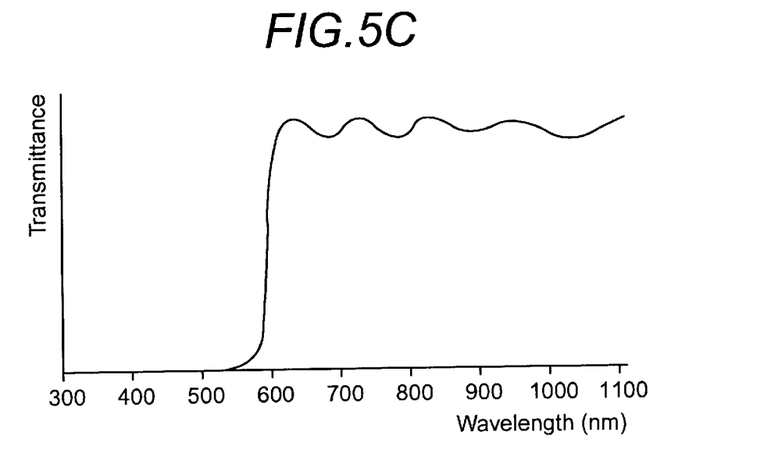

FIG. 4 is a front view of the first wheel 23. This first wheel 23 is a disc, on which three openings are formed along its circumference. Into each of these openings is fitted one of an ultraviolet-and-blue filter 231, a green filter 232 and a red filter 233. FIG. 5A is a graph showing the spectral characteristics of the ultraviolet-and-blue filter 231. As shown in this graph, the ultraviolet-and-blue filter 231 transmits ultraviolet light and blue light having wavelengths between 360 nm and 470 nm while blocking light of wavelengths between 510 nm and 750 nm. FIG. 5B is a graph showing the spectral characteristics of the green filter 232. As shown in this graph, green filter 232 transmits green light of wavelengths between 510 nm and 560 nm while blocking ultraviolet light and blue light of wavelengths between 350 nm and 470 nm and red light of wavelengths between 600 nm and 750 nm. FIG. 5C is a graph showing the spectral characteristics of the red filter 233. As shown in this graph, red filter 233 transmits red light of wavelengths between 600 nm and 700 nm to pass therethrough while blocking ultraviolet light, blue light, and green light of wavelengths between 350 nm and 560 nm. The first wheel 23 is linked with and rotated by a first motor M1. The first wheel 23 is set at a position where each of the filters 231, 232, 233 is sequentially and repeatedly inserted into the optical path of light that has passed through the light source filter 22 when rotated by the motor M1. These components, the first wheel 23 and the first motor M1, function as the first filter mechanism. Light that has passed through the above-mentioned light source filter 22 then passes through one of the filters 231, 232, and 233 of the first wheel 23 sequentially, when the ultraviolet-and-blue filter 231 is inserted into the optical path, light that has passed through the light source filter 22 is converted into light including only wavelength components in the ultraviolet spectrum and in the blue region of the visible spectrum (ultraviolet-and-blue light). Moreover, when the green filter 232 is inserted into the optical path, light that has passed through the light source filter 22 is converted into light including only wavelength components in the green region of the visible spectrum (green light). Moreover, when the red filter 233 is inserted into the optical path, light that has passed through the light source filter 22 is converted into light including only wavelength components in the red region of the visible spectrum (red light). Light that has passed through one of filters 231, 232, and 233 of the first wheel 23 is stopped down by the diaphragm 24, then travels to the second wheel 25. Incidentally, the ultraviolet-and-blue filter 231 corresponds to the first filter, the green filter 232 is the second filter, and the red filter 233 is the third filter. In addition, the blue light corresponds to the light of the first color, the green light of the second color, and red light of the third color.

Figure 6:
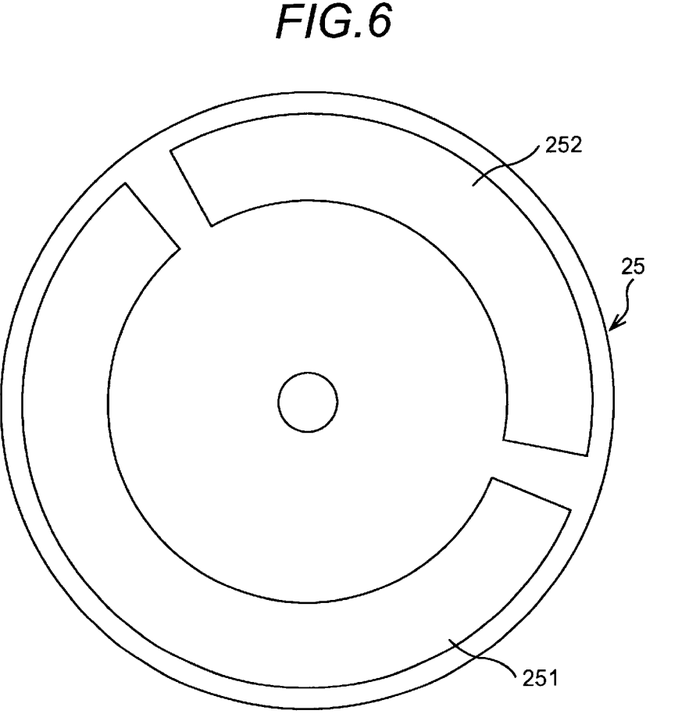
FIG. 6 is a front view of the second wheel.
Figure 7:
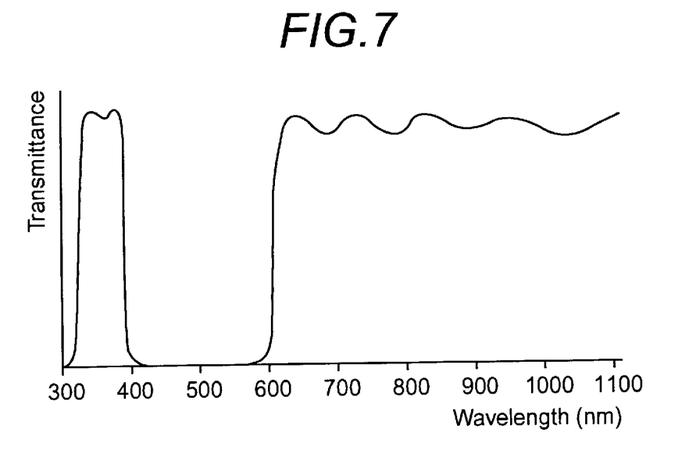
FIG. 7 is a graph showing the spectral characteristics of the fluorescence observation filter.

FIG. 6 is a front view of the second wheel 25. This second wheel 25 is a disc, on which two arc openings are formed along its circumference. Incidentally, the length of one of the two openings along the circumference is twice as long as the length of the other opening. A transparent member 251 is fitted into the opening having a longer length along the circumference. This transparent member 251 is made of white glass that almost transmits light of the visible and ultraviolet spectra. Alternatively, this opening may be a mere simple aperture with no transparent member 251 fitted thereinto. A fluorescence observation filter 252 is fitted into the other opening in this second wheel 25. FIG. 7 is a graph showing the spectral characteristics of the fluorescence observation filter 252. As shown in this graph, the fluorescence observation filter 252 transmits ultraviolet light of wavelengths between 360 nm and 380 nm and red light of wavelengths between 600 nm and 700 nm, while blocking light of wavelengths between 400 nm and 580 nm. This second wheel 25 is linked with and rotated by a motor M2. Note that this second wheel 25 is set at a position where the transparent member 251 and the fluorescence observation filter 252 is sequentially and repeatedly inserted into the optical path of light that has been stopped down by the diaphragm 24 when rotated by the motor M2. These components, the second wheel 25 and the second motor M2, function as the second filter mechanism. Light that has passed through the transparent member 251 or the fluorescence observation filter 252 in this second wheel 25 enters a condenser lens 26. The condenser lens 26 converges the incident light (collimated light beam) onto the proximal end face of the light guide 13.

Further, the external unit 2 has a control part 27 and an image processing part 28 that are connected to each other. Incidentally, these parts, the control part 27 and the image processing part 28, function as the processor. The control part 27 is connected to the motors M1, M2, respectively. Further, the control part 27 rotates the first motor M1 with an angular velocity three times as fast as that of the second motor M2. The image processing part 28 is connected to the CCD 15, and receives image signals output from the CCD 15 to process the signals.

Figure 8:
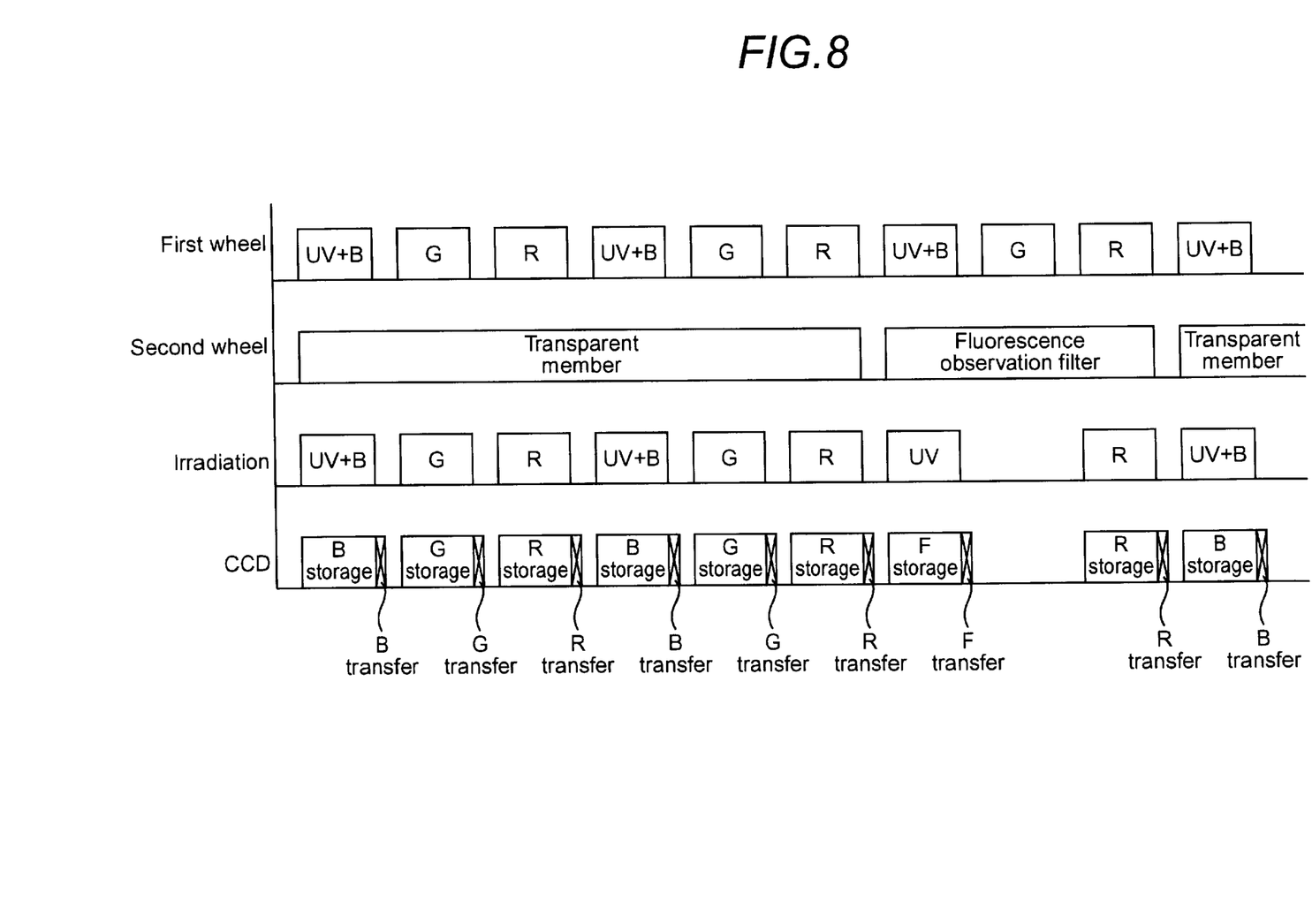
FIG. 8 is a timing chart for the irradiation of the subject and image acquisition.

FIG. 8 is a timing chart of irradiation for the subject and of image acquisition. As shown in FIG. 8, during the interval for which the second wheel 25 inserts the transparent member 251 into the optical path, the first wheel 23 makes two revolutions. As a result, during this time, ultraviolet-and-blue light (UV+B), green light (G), and red light (R), then ultraviolet-and-blue light (UV+B), green light (G), and red light (R) again are emitted from the first wheel 23 in this sequence. The amount of emitted light is adjusted by the diaphragm 24 and then the light travels to the second wheel 25. During the aforementioned period, the transparent member 251 of the second wheel 25 makes the incident light pass therethrough as it is. Light that has passed through the second wheel 25 is converged by the condenser lens 26 and enters the light guide 13. The light guided by this light guide 13 is emitted through its distal end and irradiates the subject through the light distribution lens 11. Therefore, in the aforementioned period, the subject is irradiated in order by ultraviolet-and-blue light (UV+B), green light (G), and red light (R), and by ultraviolet-and-blue light (UV+B), green light (G), and red light (R) again.

When the subject is irradiated by the ultraviolet-and-blue light (UV+B), the ultraviolet-and-blue (UV+B) light reflected by the subject surface in examination enters the objective lens 12. Note that, since the wavelength components in the ultraviolet spectrum (UV) of the ultraviolet-and-blue light (UV+B) excite living tissue to cause autofluorescence (in the green region of the visible spectrum), the autofluorescence (F) is emitted from the subject. Thus, although autofluorescence (F) emitted from the subject also enters the objective lens 12, the intensity of this autofluorescence (F) is significantly lower than the intensity of the reflected light of the ultraviolet-and-blue light (UV+B). From the light (UV+B, F) that has passed through the objective lens 12, the excitation light components (UV) are strained off by the ultraviolet-and-infrared cut-off filter 14, and the remainder thereof is focused onto the imaging plane of the CCD 15. More specifically, the image of the subject formed from blue light (B), which is the light remaining after wavelength components in the ultraviolet spectrum were eliminated from the ultraviolet-and-blue light (UV+B), is focused onto the imaging plane of the CCD 15. Note that, although the blue light also includes the autofluorescence (F) from the subject, the intensity of this fluorescence (F) is significantly lower than the intensity of the blue light (B) reflected by the subject surface. As shown in FIG. 8, the period during which the subject is irradiated by the ultraviolet-and-blue light (UV+B) corresponds to a "B storage" period for the CCD 15. Electric charges stored in the CCD 15 during this "B storage" period are sent to the image processing part 28 as a blue image signal during the subsequent "B transfer" period. Strictly speaking, this blue image signal corresponds to the image of the subject formed from the blue light (B) and the autofluorescence (F). However, as described above, since autofluorescence (F) is significantly weaker than blue light (B) reflected by the subject surface, this blue image signal virtually equals the image formed by the blue light reflected by the subject surface.

When the subject is illuminated by the green light (G), the green light (G) reflected by the subject surface in examination enters the objective lens 12. Light that has passed through this objective lens 12 then passes through the ultraviolet-and-infrared cut-off filter 14 and is focused onto the imaging plane of the CCD 15. More specifically, the image of the subject formed from the green light (G) is focused onto the imaging plane of the CCD 15. The period during which the subject is illuminated by the green light (G) corresponds to a "G storage" period for the CCD 15. Electric charges stored in the CCD 15 during the "G storage" period are sent to the image processing part 28 as a green image signal during the subsequent "G transfer" period. This green image signal corresponds to the image of the subject formed from the green light (G).

When the subject is illuminated by the red light (R), the red light (R) reflected by the subject surface in examination enters the objective lens 12. Light that has passed through the objective lens 12 then passes through the ultraviolet-and-infrared cut-off filter 14 and is focused onto the imaging plane of the CCD 15. More specifically, the image of the subject formed from the red light (R) is focused on the imaging plane of the CCD 15. The period during which the subject is illuminated by the red light (R) corresponds to a "R storage" period for the CCD 15. Electric charges stored in the CCD 15 during this "R storage" period are sent to the image processing part 28 as a red image signal during the subsequent "R transfer" period. This red image signal corresponds to the image of the subject formed from the red light (R).

On the other hand, during the period in which the second wheel 25 inserts its fluorescence observation filter 252 into the optical path, the first wheel 23 makes one revolution. As a result, during this period, ultraviolet-and-blue-light (UV+B), green light (G), and red light (R) are emitted in order from the first wheel 23. The amount of emitted light is adjusted by the diaphragm 24 and then the light travels to the second wheel 25. When the ultraviolet-and-blue light (UV+B) enters the fluorescence observation filter 252 of the second wheel 25, fluorescence observation filter 252 transmits only wavelength components in the ultraviolet spectrum (UV) in the ultraviolet-and-blue light (UV+B). Light that has passed through this fluorescence observation filter 252 is ultraviolet light (UV) used as excitation light. This ultraviolet light (UV) is converged by the condenser lens 26 and enters the light guide 13. The ultraviolet light (UV) guided by light guide 13 is emitted through the distal end face thereof and irradiates the subject through the light distribution lens 11. When irradiated by ultraviolet light (UV), this subject emits autofluorescence (F). Therefore, the autofluorescence (F) emitted from the subject and the ultraviolet light (UV) reflected by the subject in examination enter the objective lens 12.

The components of the ultraviolet light (UV) in the light that has passed through this objective lens 12 are blocked by the ultraviolet-and-infrared cut-off filter 14 and the remaining components are focused onto the imaging plane of the CCD 15. More specifically, the image of the subject formed from the autofluorescence (F) of the living tissue is focused onto the imaging plane of the CCD 15.

Incidentally, the period during which the subject is irradiated by the ultraviolet light (UV) corresponds to a "F storage" period for the CCD 15. The electric charges stored in the CCD 15 during the "F storage" period are sent to the image processing part 28 as a fluorescence image signal during a subsequent "F transfer" period. This fluorescence image signal corresponds to the subject image formed from the autofluorescence (F).

Further, during the period in which the second wheel 25 inserts its fluorescence observation filter 252 into the optical path, whenever green light (G) enter this second wheel 25, second fluorescence observation filter 252 blocks the green light (G). Therefore, the green light (G) is not transmitted to the optical path beyond the second wheel 25.

On the other hand, during the period in which the second wheel 25 inserts its fluorescence observation filter 252 into the optical path, whenever red light (R) enter this second wheel 25, the second fluorescence observation filter 252 transmits the red light (R). The red light (R) that has passed therethrough is converged by the condenser lens 26 and enters the light guide 13. The red light (R) guided by this light guide 13 is emitted through the distal end face thereof and irradiates the subject through the light distribution lens 11. Accordingly, the red light (R) reflected by this subject enters the objective lens 12.

When this subject is illuminated by the red light (R), the red light reflected by the subject surface in examination enters the objective lens 12. Light that has passed through the objective lens 12 passes through the ultraviolet-and-infrared cut-off filter 14 and is focused onto the imaging plane of the CCD 15. More specifically, the subject image formed from the red light (R) on the imaging plane of the CCD 15.

Incidentally, the period during which this subject is illuminated by the red light (R) corresponds to an "R storage" period for the CCD 15. Electric charges stored in the CCD 15 during this "R storage" period are sent to the image processing part 28 as a red image signal during a subsequent "R transfer" period. The red image signal thus obtained is used as a reference image for image processing, as described later.

Figure 9:
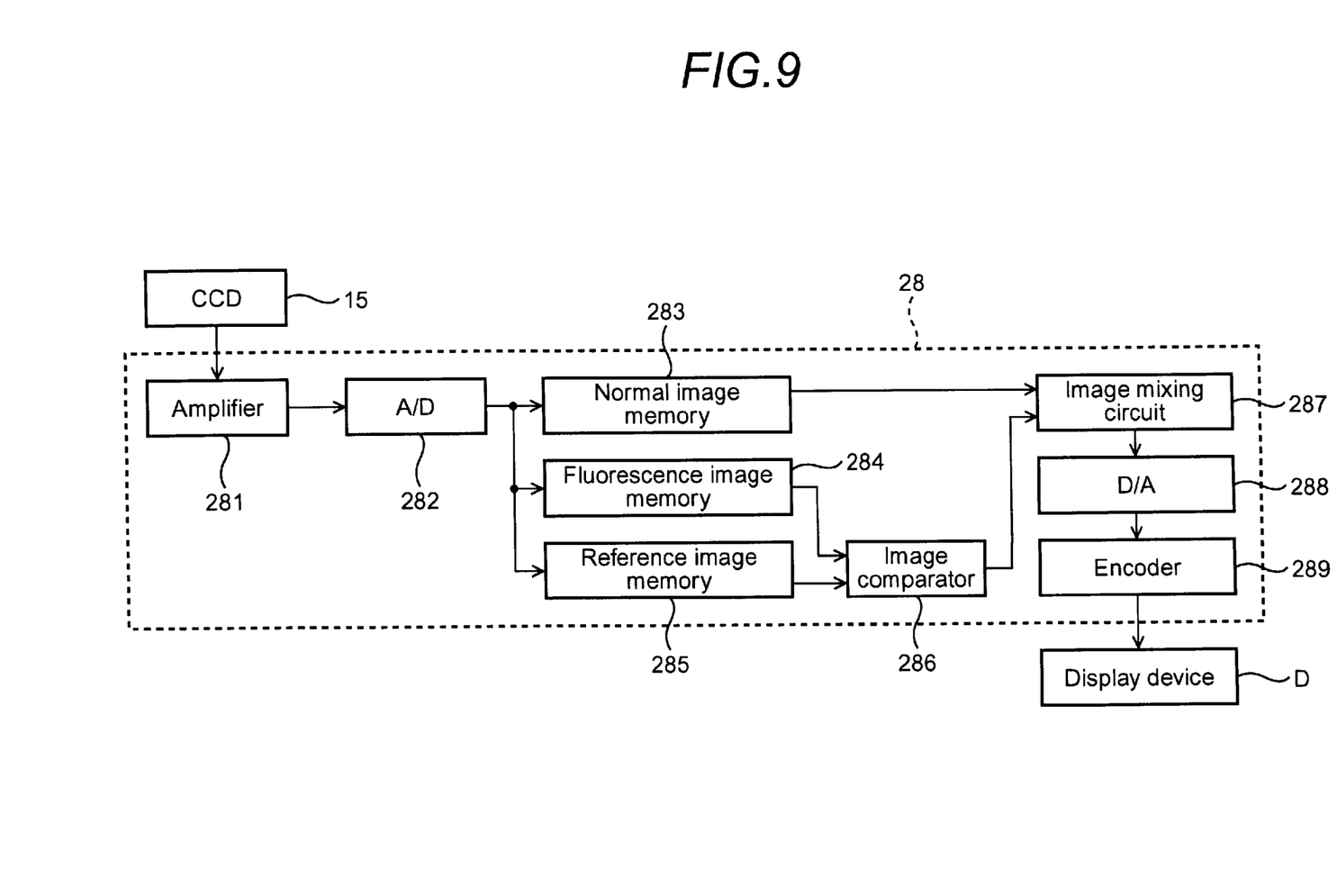
FIG. 9 is an outline block diagram showing the inner structure of an image processing part.

FIG. 9 is an schematic block diagram showing the structure of the image processing part 28. As shown in FIG. 9, the image processing part 28 has an amplifier 281, an A/D converter 282, a normal image memory 283, a fluorescence image memory 284 and a reference image memory 285.

During the period in which the second wheel 25 inserts its transparent member 251 into the optical path, blue, green and red image signals sent from the CCD 15 are amplified by the amplifier 281 at a predetermined normal amplification factor. The amplified signals are A/D-converted by the A/D converter 282 and stored in the normal image memory 283 as normal image data. Specifically, this normal image data is stored in the normal image memory 283 as color image data of a predetermined number of pixels.

On the other hand, during the period in which the second wheel 25 inserts its fluorescence observation filter 252 into the optical path, the fluorescence image signal and the red image signal sent from the CCD 15 are forwarded to the amplifier 281. The amplifier 281 amplifies the fluorescence image signal at a predetermined fluorescence amplification factor. The amplified signal is A/D-converted by the A/D converter 282 and stored in the fluorescence image memory 284 as fluorescence image data. Since the fluorescence image signal is weaker than other image signals, the fluorescence amplification factor is set to be greater than the normal amplification factor. The fluorescence image data is stored in the fluorescence image memory 284 as monochrome image data of a predetermined number of pixels.

Further, the amplifier 281 amplifies the red image signal at a predetermined reference amplification factor. This reference amplification factor is set to be a predetermined value larger than the normal amplification factor but smaller than the fluorescence amplification factor. The amplified signal is A/D-converted by the A/D converter 282 and stored in the reference image memory 285 as reference image data. This reference image data is stored in the reference image memory 285 as monochromatic image data of a predetermined number of pixels. Incidentally, the brightness value of this reference image data is set to be equivalent to the brightness value of the fluorescence image data.

Further, image processing part 28 has an image comparator 286, an image mixing circuit 287, a D/A converter 288 and an encoder 289. Image comparator 286 is connected to the fluorescence image memory 284 and the reference image memory 285. The image comparator 286 reads both the fluorescence image data in the fluorescence image memory 284 and the reference image data in the reference image memory 285, and then subtracting the reference image data from the fluorescence image data to generate specific image data. This specific image data includes only information that corresponds to areas of the subject that are potentially abnormal (areas where autofluorescence is weak).

The image mixing circuit 287 is connected to the normal image memory 283 and the image comparator 286. The image mixing circuit 287 reads both the normal image data in the normal image memory 283 and the specific image data generated in the image comparator 286. This image mixing circuit 287 generates diagnostic image data by superimposing the specific image data of a specific color (e.g., blue) upon the normal image data, and outputs this diagnostic image data.

The D/A converter 288 is connected to an image mixing circuit 287. The D/A converter 288 also outputs diagnostic image signal by D/A converting the diagnostic image data output from the image mixing circuit 287.

The encoder 289 is connected to the D/A converter 288 and also to the display device D, that is a television monitor, a personal computer, or other similar device. The encoder 289 receives the diagnostic image signal output from the D/A converter 288, adds signals used to implement screen display on the display device D (e.g., synchronization signals) to this diagnostic image signal, and outputs it. The display device D displays the diagnostic image as moving picture based on signals output from the encoder 289. Optionally, the display device D may display a normal image based on the normal image data alongside the diagnostic image side by side.

Figure 10:
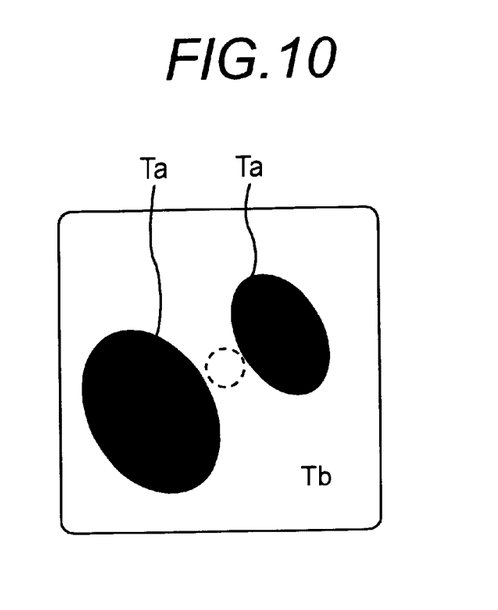
FIG. 10 is a schematic view of the normal image and the reference image.
Figure 11:
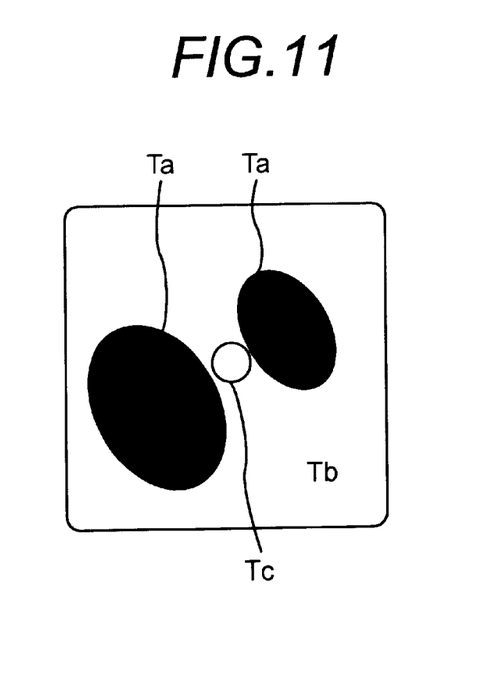
FIG. 11 is a schematic view of the fluorescence image.

FIG. 10 is a schematic view of the normal image being displayed based on the normal image data stored in the normal image memory 283. FIG. 11 is a schematic view of the fluorescence image being displayed, based on the fluorescence image data stored in the fluorescence image memory 284. In these normal and fluorescence images, lumen Ta appears dark due to an absence of reflection nor autofluorescence, whereas luminal wall Tb appears bright. Further, the fluorescence image of FIG. 11 shows diseased tissue Tc in luminal wall Tb, where autofluorescence is weak. Incidentally, the reference image data stored in the reference image memory 285 is almost equivalent to the components of the red image signal data in the normal image data. Thus, FIG. 10 is also a schematic view of the reference image being displayed based on this reference image data. However, normal image data is actually color image data, whereas the reference image data is monochromatic.

Figure 12:
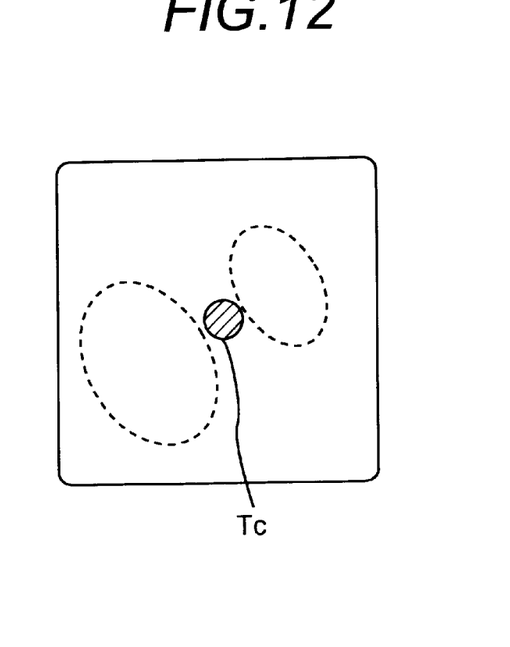
FIG. 12 is a schematic view of a specific image.

FIG. 12 is a schematic view of the specific image being displayed based on the specific image data output from the image comparator 286. This specific image (FIG. 12) is obtained by subtracting the reference image (FIG. 10) from the fluorescence image (FIG. 11). As shown in FIG. 12, this specific image includes only diseased tissue Tc, and does not include healthy portions of the luminal wall Tb or the lumen Ta.

Figure 13:
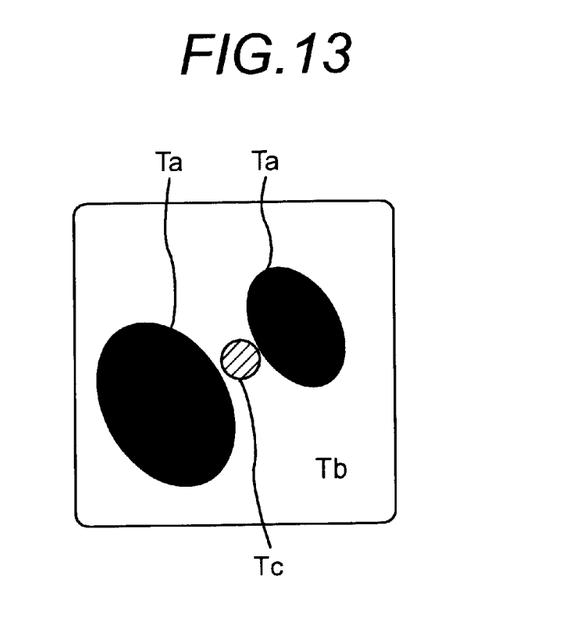
FIG. 13 is a schematic view of a diagnostic image.

FIG. 13 is a schematic view of the diagnostic image being displayed based on diagnostic image data output from the image mixing circuit 287. This diagnostic image (FIG. 13) is obtained by superimposing the specific image (FIG. 12) upon the normal image (FIG. 10). In this diagnostic image, diseased tissue Tc is colored blue or another color. This gives the operator the means to recognize the location and shape of abnormal tissue Tc correctly through inspection of the diagnostic image displayed on the screen of the display device D.

The operator can also treat diseased tissue Tc while inspecting the diagnostic image. For example, the operator may perform laser therapy by irradiating this diseased tissue Tc with infrared laser light from a laser probe which is led through a forceps channel (not shown in this figure) to the distal end of endoscope 1. Incidentally, infrared light emitted from the laser probe enters the objective lens 12 of the endoscope 1 following reflection by the subject. However, since infrared light that has passed through this objective lens 12 is blocked by the ultraviolet-and-infrared cut-off filter 14, it does not reach the CCD 15. Therefore, even during laser therapy, the image displayed on the display device D is displayed normally.

As described in the foregoing, this endoscope system can direct both illumination light and irradiation light, both of which are required to acquire the color normal image and the diagnostic image respectively, to the light guide 13 by using a single light source 21. This reduces power consumption compared to configurations involving multiple light sources. In addition, since this endoscope has a simpler configuration compared to the devices containing multiple light sources, the overall device can be minimized and its costs can be reduced.

What is claimed is:

1. An endoscope system, comprising:
    a light source for emitting light including visible wavelength components and an ultraviolet wavelength component to excite autofluorescence from living tissue;
    a light guide that is arranged along an optical path of the light emitted from said light source, for guiding the light to irradiate a subject;
    a first filter mechanism that has a first filter transmitting the ultraviolet light and first color light which is one of blue, green and red light, a second filter transmitting second color light which is one of the blue, green and red light other than the first color light, and a third filter transmitting third color light which is remain of the blue, green and red light, said first filter mechanism sequentially and repeatedly inserting said filters into the optical path between said light source and said light guide;
    a second filter mechanism that intermittently inserts a fluorescence observation filter transmitting ultraviolet light, while blocking said first color light into the optical path between said light source and said light guide;
    an objective optical system that focuses wavelength components except ultraviolet light from the subject irradiated by said light guide to form an image of the subject;
    an imaging device that picks up the image of the subject formed by said objective optical system to convert them into image signals; and a processor that generates normal image data that is color image data, based on the image signals obtained by said imaging device during a period for which said first filter is inserted into the optical path, during a period for which said second filter is inserted into the optical path, and during a period for which said third filter is inserted into the optical path, respectively, while controlling said first filter mechanism with said fluorescence observation filter retracted from the optical path, generates fluorescence image data based on the image signals obtained by said imaging device during a period for which said first filter is inserted into the optical path while controlling said first filter mechanism with said fluorescence observation filter inserted into the optical path.

2. An endoscope system according to claim 1, wherein said fluorescence observation filter transmits only ultraviolet light and one of said second color light and said third color light, and wherein said processor generates reference image data based on the image signals obtained by said imaging device during a period for which said second filter or third filter transmitting said second or third color light is inserted into the optical path, by controlling said first filter mechanism with said fluorescence observation filter inserted into the optical path, extracts specific image data by subtracting said reference image data from said fluorescence image data, and generates diagnostic image data by superimposing said specific image data on said normal image data.

3. An endoscope system according to claim 1, wherein said first filter mechanism has a first wheel in discal shape, on which said first filter, second filter and third filter are fitted along its circumference so as to be sequentially inserted into said optical path by rotation of the first wheel.

4. An endoscope system according to claim 1, wherein said second filter mechanism has a second wheel in discal shape, on which said fluorescence observation filter and an opening are provided along its circumference so as to be sequentially inserted into said optical path by rotation of the second wheel.

5. An endoscope system according to claim 1, wherein said processor generates each image data as video data.

6. An endoscope system according to claim 1, wherein said first color light is blue light.

7. An endoscope system according to claim 1, further comprising a display device capable of displaying each image data generated by said processor.

* * * * *